United States Patent
Schneider et al.

(10) Patent No.: US 10,507,340 B2
(45) Date of Patent: Dec. 17, 2019

(54) ORAL CARE PRODUCTS AND METHODS COMPRISING AFPS

(71) Applicant: BASF SE, Ludwigshafen am Rhein (DE)

(72) Inventors: Nina Schneider, Edingen-Neckarhausen (DE); Thomas Subkowski, Schriesheim (DE); Stefan Jenewein, Neustadt (DE); Marvin Karos, Plankstadt (DE); Claus Bollschweiler, Heidelberg (DE); Volker Wendel, Seeheim-Jugenheim (DE); Jianhong Qiu, Warren, NJ (US); LaTonya Kilpatrick-Liverman, Princeton, NJ (US); Lynette Zaidel, Cranford, NJ (US)

(73) Assignee: BASF SE, Ludwigshafen (DE)

(*) Notice: Subject to any disclaimer, the term of this patent is extended or adjusted under 35 U.S.C. 154(b) by 29 days.

(21) Appl. No.: 15/770,978

(22) PCT Filed: Oct. 25, 2016

(86) PCT No.: PCT/EP2016/075649
§ 371 (c)(1),
(2) Date: Apr. 25, 2018

(87) PCT Pub. No.: WO2017/072104
PCT Pub. Date: May 4, 2017

(65) Prior Publication Data
US 2019/0022429 A1    Jan. 24, 2019

Related U.S. Application Data

(60) Provisional application No. 62/246,163, filed on Oct. 26, 2015.

(51) Int. Cl.
| | | |
|---|---|---|
| A61Q 11/00 | (2006.01) | |
| A61K 8/21 | (2006.01) | |
| A61K 8/64 | (2006.01) | |
| A61K 9/68 | (2006.01) | |

(52) U.S. Cl.
CPC ............ *A61Q 11/00* (2013.01); *A61K 8/21* (2013.01); *A61K 8/64* (2013.01); *A61K 9/0058* (2013.01)

(58) Field of Classification Search
None
See application file for complete search history.

(56) References Cited

U.S. PATENT DOCUMENTS

| | | |
|---|---|---|
| 2003/0180884 A1 | 9/2003 | Hoshino et al. |
| 2006/0008440 A1 | 1/2006 | Blatt et al. |
| 2013/0165626 A1 | 6/2013 | Fukuoka et al. |

FOREIGN PATENT DOCUMENTS

| | | |
|---|---|---|
| CN | 102108357 A | 6/2011 |
| EP | 2409682 A1 | 1/2012 |
| WO | WO-2004/022081 A1 | 3/2004 |
| WO | WO-2012/023486 A1 | 2/2012 |
| WO | WO-2012/166626 A1 | 12/2012 |

OTHER PUBLICATIONS

Duman, Animal ice-binding (antifreeze) proteins and glycolipids: an overview with emphasis on physiological function, J. Exp. Biol., vol. 218, 2015, pp. 1846-1855.
European Patent Application No. 16157196.3, Search Report, dated Aug. 1, 2016, 3 pages.
International Patent Application No. PCT/EP2016/075649, International Preliminary Report on Patentability, dated May 1, 2018, 6 pages.
International Patent Application No. PCT/EP2016/075649, International Search Report and Written Opinion, dated Feb. 13, 2017, 4 pages.
Venketesh et al., Properties, Potentials, and Prospects of Antifreeze Proteins, Crit. Rev. Biotechnol., vol. 28, Issue 1, 2018, pp. 57-82.

*Primary Examiner* — Manjunath N Rao
*Assistant Examiner* — Jae W Lee
(74) *Attorney, Agent, or Firm* — Marshall, Gerstein & Borun LLP

(57) ABSTRACT

Provided herein are oral care compositions comprising antifreeze proteins (AFPs) useful in methods of repairing or inhibiting dental erosion, promoting dental remineralization, and/or enhancing the anti-cavity effects of fluoride.

10 Claims, 5 Drawing Sheets
Specification includes a Sequence Listing.

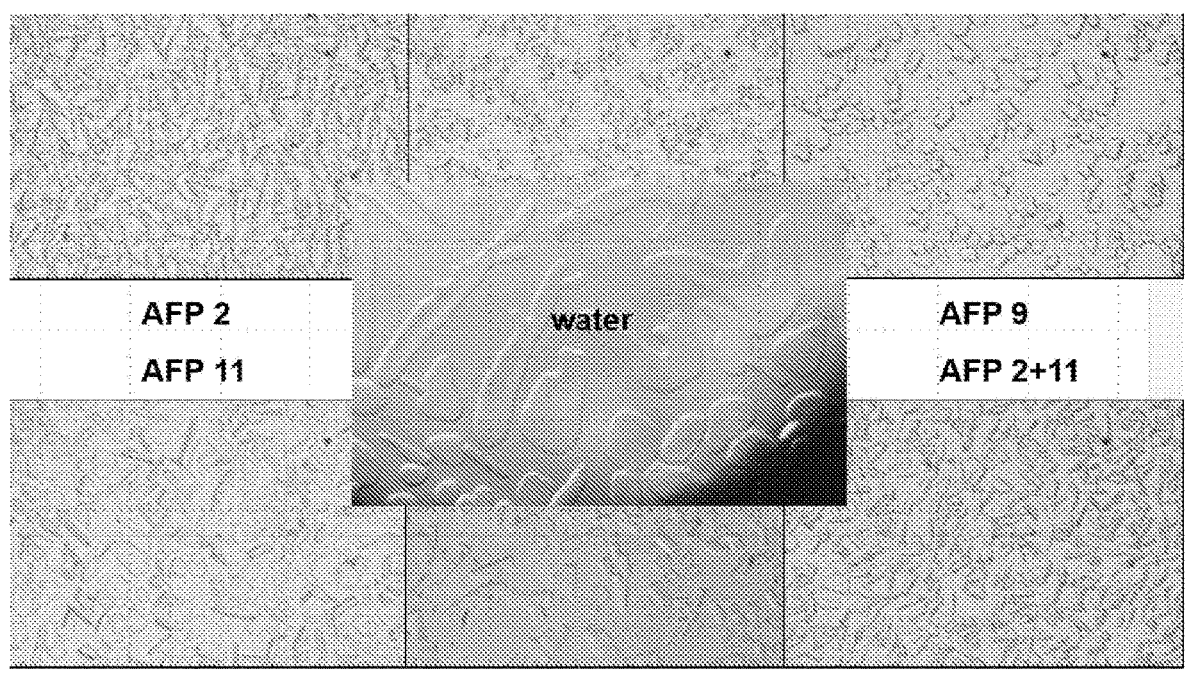
Fig.1 ice crystal formation in the presence and absence of AFP

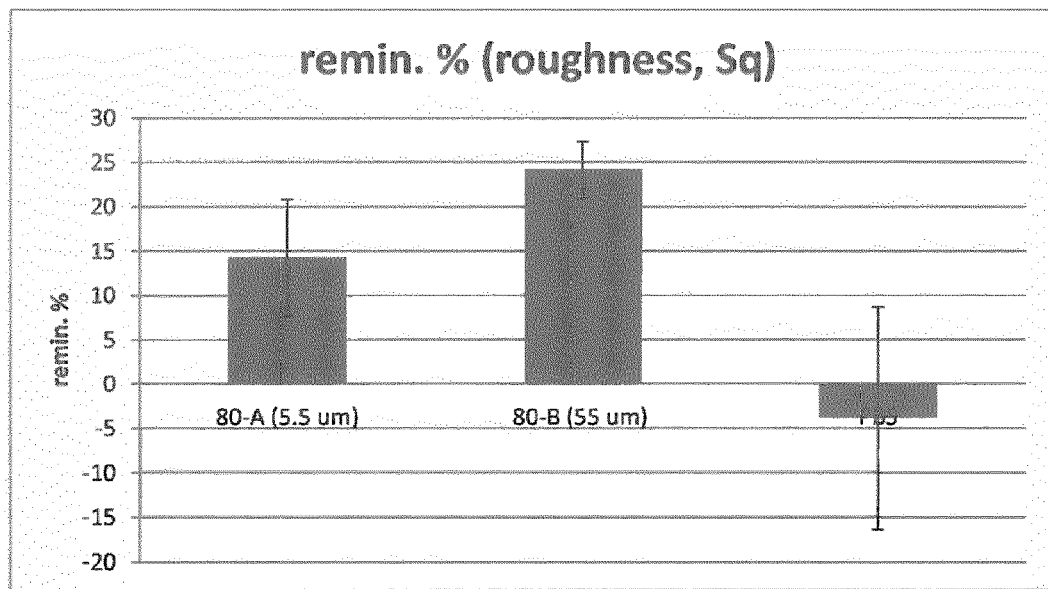
Figure 2: Repair efficacy of BM 80 on low (5.5 µM) and high (55 µM) concentration using roughness assay.

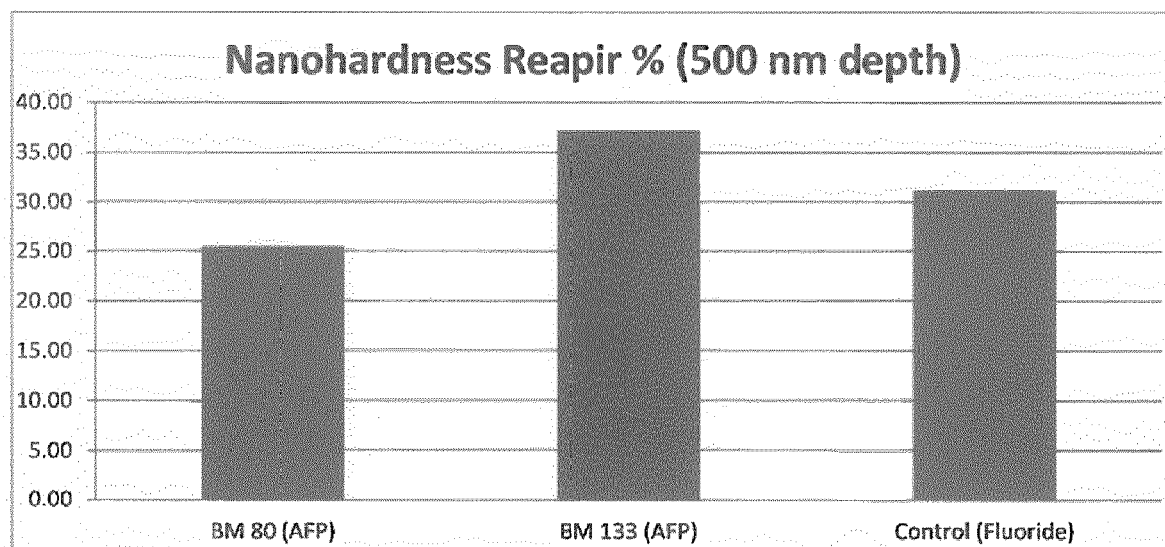
Figure 3: Repair efficacy (nanohardness) of AFP using nanoindentation

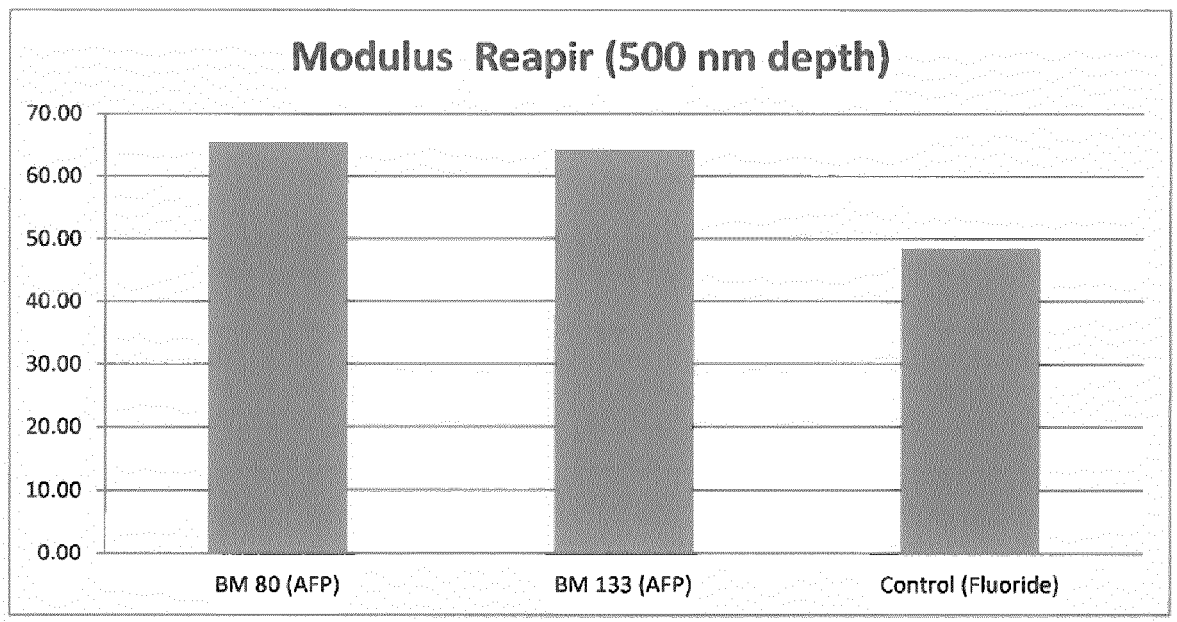
Figure 4: Repair efficacy (Young's modulus) of AFP using nanoindentation

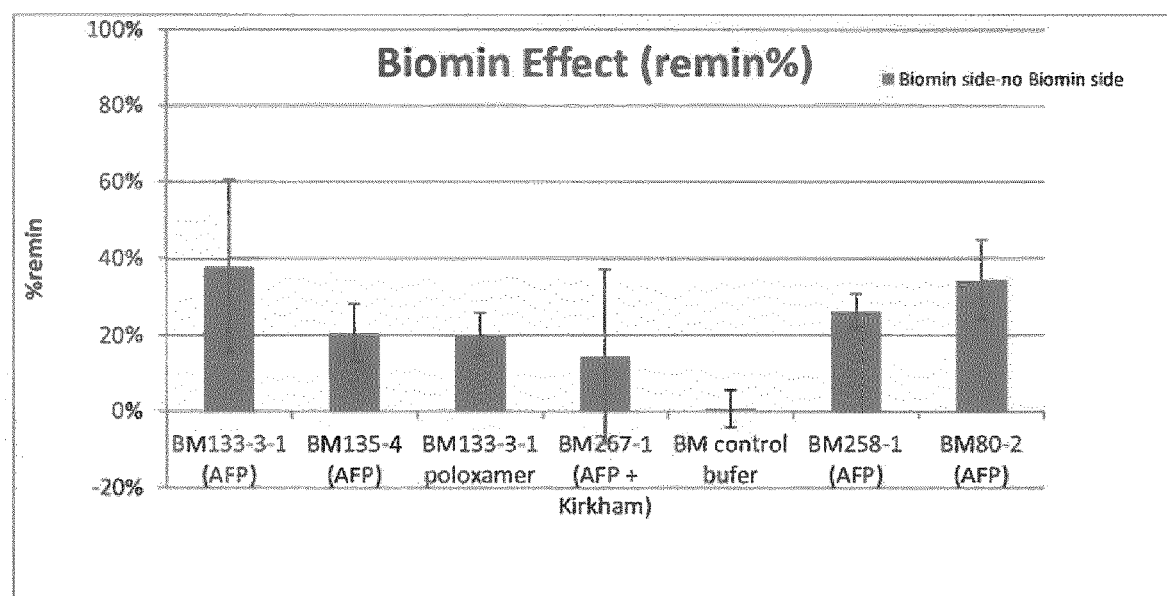
Figure5. Repair efficacy of AFP using microhardness

SEQUENCE LISTING

<160> NUMBER OF SEQ ID NOS: 21

<210> SEQ ID NO 1
<211> LENGTH: 178
<212> TYPE: PRT
<213> ORGANISM: Zoarces americanus

<400> SEQUENCE: 1

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Val Ile Leu His His
                20                  25                  30

Lys Val Tyr Asp Leu Thr Lys Phe Leu Glu Glu His Pro Gly Gly Glu
            35                  40                  45

Glu Val Leu Gly Glu Gln Ala Gly Gly Asp Ala Thr Glu Asn Phe Glu
        50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95

Glu Thr Leu Asp Asp Asp Lys His Met Asn Gln Ala Ser Val Val
                100                 105                 110

Ala Asn Gln Leu Ile Pro Ile Asn Thr Ala Leu Thr Leu Val Met Met
            115                 120                 125

Arg Ser Glu Val Val Thr Pro Val Gly Ile Pro Ala Glu Asp Ile Pro
        130                 135                 140

Arg Leu Val Ser Met Gln Val Asn Arg Ala Val Pro Leu Gly Thr Thr
145                 150                 155                 160

Leu Met Pro Asp Met Val Lys Gly Tyr Pro Pro Ala His His His His
                165                 170                 175

His His

<210> SEQ ID NO 2
<211> LENGTH: 97
<212> TYPE: PRT
<213> ORGANISM: Choristoneura fumiferana -continued

<400> SEQUENCE: 2

Met Asp Gly Ser Cys Thr Asn Thr Asn Ser Gln Leu Ser Ala Asn Ser
1               5                   10                  15

Lys Cys Glu Lys Ser Thr Leu Thr Asn Cys Tyr Val Asp Lys Ser Glu
            20                  25                  30

Val Tyr Gly Thr Thr Cys Thr Gly Ser Arg Phe Asp Gly Val Thr Ile
        35                  40                  45

Thr Thr Ser Thr Ser Thr Gly Ser Arg Ile Ser Gly Pro Gly Cys Lys
    50                  55                  60

Ile Ser Thr Cys Ile Ile Thr Gly Gly Val Pro Ala Pro Ser Ala Ala
65                  70                  75                  80

Cys Lys Ile Ser Gly Cys Thr Phe Ser Ala Asn His His His His His
                85                  90                  95

His

<210> SEQ ID NO 3
<211> LENGTH: 317
<212> TYPE: PRT
<213> ORGANISM: Lolium perenne

<400> SEQUENCE: 3

Met Thr Thr Gln Ser Pro Leu Asn Ser Phe Tyr Ala Thr Gly Thr Ala
1               5                   10                  15

Gln Ala Val Ser Glu Pro Ile Asp Val Glu Ser His Leu Gly Ser Ile
            20                  25                  30

Thr Pro Ala Ala Gly Ala Gln Gly Ser Asp Asp Ile Gly Tyr Ala Ile
        35                  40                  45

Val Trp Ile Lys Asp Gln Val Asn Asp Val Lys Leu Lys Val Thr Leu
    50                  55                  60

Arg Asn Ala Glu Gln Leu Lys Pro Tyr Phe Lys Tyr Leu Gln Ile Gln
65                  70                  75                  80

Ile Thr Ser Gly Tyr Glu Thr Asn Ser Thr Ala Leu Gly Asn Phe Ser
                85                  90                  95

Glu Thr Lys Ala Val Ile Ser Leu Asp Asn Pro Ser Ala Val Ile Val
            100                 105                 110

Leu Asp Lys Glu Asp Ile Ala Val Leu Tyr Pro Asp Lys Thr Gly Tyr
        115                 120                 125

Thr Asn Thr Ser Ile Trp Val Pro Gly Glu Pro Asp Lys Ile Ile Val
    130                 135                 140

Tyr Asn Glu Thr Lys Pro Val Ala Ile Leu Asn Phe Lys Ala Phe Tyr
145                 150                 155                 160

Glu Ala Lys Glu Gly Met Leu Phe Asp Ser Leu Pro Val Ile Phe Asn
                165                 170                 175

Phe Gln Val Leu Gln Val Gly Gly Ser Gly Gly Asp Pro Gly Gly
            180                 185                 190

Met Asp Glu Gln Pro Asn Thr Ile Ser Gly Ser Asn Asn Thr Val Arg
        195                 200                 205

Ser Gly Ser Lys Asn Val Leu Ala Gly Asn Asp Asn Thr Val Ile Ser
    210                 215                 220

Gly Asp Asn Asn Ser Val Ser Gly Ser Asn Asn Thr Val Val Ser Gly
225                 230                 235                 240

Asn Asp Asn Thr Val Thr Gly Ser Asn His Val Val Ser Gly Thr Asn
                245                 250                 255

```
His Ile Val Thr Asp Asn Asn Asn Val Ser Gly Asn Asp Asn Asn
            260                 265                 270

Val Ser Gly Ser Phe His Thr Val Ser Gly Gly His Asn Thr Val Ser
        275                 280                 285

Gly Ser Asn Asn Thr Val Ser Gly Ser Asn His Val Val Ser Gly Ser
        290                 295                 300

Asn Lys Val Val Thr Asp Ala His His His His His His
305                 310                 315

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Ile Asp Asp Tyr Thr Arg Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

His Pro Pro Leu His His Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Ser Pro Ser Thr His Trp Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Gly Ser His Ala Thr Ala Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Gly Lys Val Gln Ala Gln Ser
1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Tyr Pro Val Thr Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Ile Pro Thr Leu Pro Ser Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Tyr Gln Gly Ala Ser Glu Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Glu His Ile Thr Thr Ser Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Arg Ile Leu Ile Thr Ile Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Ile Pro Ile Thr Asn Leu Arg
1               5
```

```
<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Thr Thr Ser Thr Arg His Ile
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 16

Asn Glu Arg Ala Leu Thr Leu
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 17

Met Gln Thr Val Glu Val Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Ser Trp Gly Thr Gln Thr Asp
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Thr Leu Pro Ala Ser Ser Val
1               5

<210> SEQ ID NO 20
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 20

Met Ile Asp Asp Tyr Thr Arg Ala Gly Gly Gly Asp Gly Ser Cys Thr
1               5                   10                  15

Asn Thr Asn Ser Gln Leu Ser Ala Asn Ser Lys Cys Glu Lys Ser Thr
            20                  25                  30
```

```
Leu Thr Asn Cys Tyr Val Asp Lys Ser Glu Val Tyr Gly Thr Thr Cys
        35                  40                  45

Thr Gly Ser Arg Phe Asp Gly Val Thr Ile Thr Thr Ser Thr Ser Thr
    50                  55                  60

Gly Ser Arg Ile Ser Gly Pro Gly Cys Lys Ile Ser Thr Cys Ile Ile
65                  70                  75                  80

Thr Gly Gly Val Pro Ala Pro Ser Ala Ala Cys Lys Ile Ser Gly Cys
                85                  90                  95

Thr Phe Ser Ala Asn His His His His His
            100                 105

<210> SEQ ID NO 21
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 21

Met Ile Pro Thr Leu Pro Ser Ser Gly Gly Asp Gly Ser Cys Thr
1               5                   10                  15

Asn Thr Asn Ser Gln Leu Ser Ala Asn Ser Lys Cys Glu Lys Ser Thr
            20                  25                  30

Leu Thr Asn Cys Tyr Val Asp Lys Ser Glu Val Tyr Gly Thr Thr Cys
        35                  40                  45

Thr Gly Ser Arg Phe Asp Gly Val Thr Ile Thr Thr Ser Thr Ser Thr
    50                  55                  60

Gly Ser Arg Ile Ser Gly Pro Gly Cys Lys Ile Ser Thr Cys Ile Ile
65                  70                  75                  80

Thr Gly Gly Val Pro Ala Pro Ser Ala Ala Cys Lys Ile Ser Gly Cys
                85                  90                  95

Thr Phe Ser Ala Asn His His His His His
            100                 105
```

ORAL CARE PRODUCTS AND METHODS COMPRISING AFPS

This application is a National Stage application of International Application No. PCT/EP2016/075649, filed Oct. 25, 2016, which claims the benefit of U.S. Patent Application No. 62/246,163, filed on Oct. 26, 2015.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "78606 SubSeqlisting.txt", which was created on Sep. 14, 2018 and is 10,420 bytes in size. The subject matter of the Sequence Listing is incorporated herein in its entirety by reference.

BACKGROUND

Dental enamel is a thin, hard layer of calcified material that covers the crown of teeth. The major mineral component of dental enamel is hydroxyapatite, a crystalline form of calcium phosphate. Chemical erosion of dental enamel may arise from tooth exposure to acidic food and drinks or to stomach acids arising from gastric reflux. The erosion of dental enamel can lead to enhanced tooth sensitivity due to increased exposure of the dentin tubules and increased dentin visibility leading to the appearance of more yellow teeth. The salivary pellicle (a thin layer of salivary glycoproteins deposited on teeth) is integral in protecting the teeth against an erosive challenge. As a result, people that experience xerostomia are more susceptible to acid erosion damage.

Existing methods developed to help prevent enamel erosion include incorporating a source of free fluoride into oral care compositions. Fluoride reduces damage to the enamel, through the formation of fluorapatite, which dissolves at a lower pH than hydroxyapatite and so is more resistant to acid damage. Stannous salts have also been incorporated into dentifrice formulations to protect the enamel surface similarly, by forming a more acid resistant mineral layer. Polymers have also been described that coat and protect the enamel surface.

Acids are also generated in the oral cavity when plaque containing cariogenic bacteria metabolize carbohydrates. Since plaque forms a barrier controlling the kinetics of proton and mineral diffusion through the enamel, plaque acids cause carious lesions. Incorporating fluoride ions in dentifrice formulations is the most common method to mitigate the effects of plaque acids. Fluoride reduces the rate of demineralization and enhances remineralization. Several approaches have also been developed to stabilize calcium phosphate salts or control the plaque pH to enhance remineralization.

Although methods have been developed to mitigate the effects of non-bacteria and bacteria generated acids on the teeth, there is still the need to provide improved oral care compositions that effectively repair the enamel from the effects of acid erosion and bacteria acids.

BRIEF SUMMARY

The present inventors have unexpectedly found that Anti Freeze Proteins (AFPs) are effective in repairing or mitigating the effects of dental erosion, promoting dental remineralization, and enhancing the anti-cavity effects of fluoride.

For example, in one embodiment, AFPs are prepared for formulation with ingredients of a suitable orally acceptable carrier, by diluting in buffer, e.g., a phospate buffer such as Na2HPO4 buffer (1.5 mM) and $CaCl_2$) (2.5 mM), to provide a buffered solution having approximately neutral or slightly basic pH, e.g., pH 7-8, e.g., about pH 7.5, filtering and centrifuging the solution to obtain a filtrat comprising the AFP. A biocide (for example cetylpyridinium chloride at 0.1%) and fluoride may be added to the filtrate. The AFP may then be combined with components of an orally acceptable carrier, for example a toothpaste or mouthwash base, to provide an oral care composition for repairing or mitigating the effects of dental erosion, promoting dental remineralization, and enhancing the anti-cavity effects of fluoride.

This disclosure thus relates to an oral care composition (Composition 1 or 2 or 3), for example a dentifrice, comprising:
a) AFP;
b) an orally acceptable carrier,
   wherein the AFP is present in the composition in an amount of from 0.01 weight % to 3 weight % by total weight of the composition. For example, the disclosure provides:
1.1. Composition 1 wherein the AFP is an insect AFP.
1.2. Composition 1 wherein the AFP has a polypeptide sequence SEQ ID NO:2.
1.3. Composition 2 wherein the AFP is an plant AFP.
1.4. Composition 2 wherein the AFP has a polypeptide sequence SEQ ID NO:3 . . . .
1.5. Composition 3 wherein the AFP is an fish AFP.
1.6. Composition 3 wherein the AFP has a polypeptide sequence SEQ ID NO:1 . . . .
1.7. Any foregoing Composition comprising fluoride.
1.8. Any foregoing Composition wherein the AFP has been neutralized to approximately neutral or slightly basic pH, e.g., pH 7-8, e.g., using a phosphate buffer.
1.9. Any foregoing Composition wherein the AFP comprises a biocide, e.g., cetylpyridinium chloride (CPC) at an effective concentration, e.g., 0.1% by weight of the filtrate.
1.10. Any foregoing Composition wherein the AFP is present in the composition in an amount of from 0.01 weight % to 3 weight % by total weight of the composition, e.g., 0.01 weight % to 2 weight %, e.g., about 0.02 weight %, about 0.1 weight %, about 0.5 weight % or about 2 weight percent by total weight of the composition.
1.11. Any foregoing composition wherein the Composition comprises an effective amount of fluoride.
1.12. Any foregoing Composition which comprises an amount of fluoride of 100 ppm to 2500 ppm, for example, 250 ppm to 750 ppm, for example about 500 ppm fluoride.
1.13. Any foregoing Composition comprising an orally acceptable zinc salt or oxide, for example selected from zinc oxide, zinc citrate, zinc lactate, zinc phosphate, zinc acetate, zinc chloride, zinc complexes with amino acids, and mixtures of any of the foregoing, for example wherein the amount of zinc is from 0.1 weight % to 3 weight %, e.g., about 1 to about 2 weight %, calculated by weight of zinc ion.
1.14. Any foregoing Composition comprising an orally acceptable stannous salt, for example $SnF_2$ or $SnCl_2$.
1.15. Any foregoing Composition wherein the composition is in a form selected from a mouthrinse, a toothpaste, a tooth gel, a tooth powder, a non-abrasive gel, a mousse, a foam, a mouth spray, and a tablet, for example dentifrice, e.g., a toothpaste or mouthrinse.

1.16. Any foregoing Composition, wherein the composition further comprises one or more agents selected from: abrasives, pH modifying agents, surfactants, foam modulators, thickening agents, viscosity modifiers, humectants, anti-calculus or tartar control agents, sweeteners, flavorants and colorants.

1.17. Any foregoing Composition wherein the composition is a toothpaste.

1.18. Any foregoing Composition comprising one or more soluble phosphate salts, for example wherein by "soluble phosphate salts" is meant an orally acceptable phosphate salt having a solubility in water of at least 1 g/100 ml at 25° C.; for example wherein the one or more soluble phosphate salts are sodium and/or potassium salts of pyrophosphates and/or polyphosphates, e.g., tripolyphosphates; e.g., wherein the one or more soluble phosphate salts comprise tetrasodium pyrophosphate (TSPP), sodium tripolyphosphate (STPP) or a combination of TSPP and STPP; for example, whereon the one or more soluble phosphate salts are present in an amount of 1-20%, e.g., 2-8%, e.g., ca. 5%, by weight of the composition.

1.19. Any foregoing Composition wherein the fluoride is provided by a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.20. Any foregoing Composition which is a dentifrice comprising a humectant, e.g., selected from glycerin, sorbitol, propylene glycol, polyethylene glycol, xylitol, and mixtures thereof, e.g. comprising at least 30%, e.g., 40-50% glycerin, by weight of the composition.

1.21. Any foregoing Composition which is a dentifrice comprising one or more surfactants, e.g., selected from anionic, cationic, zwitterionic, and nonionic surfactants, and mixtures thereof, e.g., wherein the dentifrice base comprises an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS) by weight of the composition.

1.22. Any foregoing Composition which is a dentifrice comprising a zwitterionic surfactant, for example a betaine surfactant, for example cocamidopropylbetaine, e.g. in an amount of from about 0.1% to about 4.5% by weight, e.g. 0.5-2% cocamidopropylbetaine by weight of the composition 1.23. Any foregoing Composition which is a dentifrice comprising a viscosity modifying amount of one or more of polysaccharide gums, for example xanthan gum or carrageenan, silica thickener, and combinations thereof.

1.24. Any foregoing Composition which is a dentifrice comprising gum strips or fragments.

1.25. Any foregoing Composition comprising flavoring, fragrance and/or coloring.

1.26. Any foregoing Composition which is a dentifrice comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.27. Any foregoing Composition which is a dentifrice comprising a whitening agent, e.g., a selected from the group consisting of peroxides, metal chlorites, perborates, percarbonates, peroxyacids, hypochlorites, and combinations thereof; e.g. hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate).

1.28. Any foregoing Composition which is a dentifrice comprising an agent that interferes with or prevents bacterial attachment, e.g., solbrol or chitosan.

1.29. Any foregoing Composition which is a dentifrice comprising a soluble calcium salt, e.g., selected from calcium sulfate, calcium chloride, calcium nitrate, calcium acetate, calcium lactate, and combinations thereof.

1.30. Any foregoing Composition which is a dentifrice comprising a physiologically or orally acceptable potassium salt, e.g., potassium nitrate or potassium chloride, in an amount effective to reduce dentinal sensitivity.

1.31. Any foregoing Composition which is a dentifrice comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.32. Any foregoing Composition which is a dentifrice comprising a breath freshener, fragrance or flavoring.

1.33. Any of the foregoing Compositions, wherein the pH of the composition is approximately neutral, e.g., about pH 7.

1.34. Any of the forgoing compositions for use to reduce and inhibit acid erosion, clean the teeth, reduce bacterially-generated biofilm and plaque, reduce gingivitis, inhibit tooth decay and formation of cavities, and reduce dentinal hypersensitivity.

1.35. Any foregoing Composition for use in reducing, inhibiting or repairing dental enamel erosion.

1.36. Any foregoing composition for use in promoting remineralization of dental enamel.

1.37. Any foregoing composition for use in enhancing the anti-cavity effects of fluoride.

A particular novel embodiment of Composition 1 or 2 or 3 is a dentifrice comprising
a) An AFP;
b) optionally an effective amount of fluoride;
b) an orally acceptable carrier,
for example wherein the amount of AFP is 0.01 weight % to 2 weight and
for example wherein fluoride is present in an amount of 100 ppm to 1000 ppm, for example, about 500 ppm.

In a still further embodiment, an oral care composition of the invention is a chewing gum comprising gum base, flavor, sweetening agent and AFP. The gum base is present from about 4.8% to about 90%, the flavor from about 0.1% to about 10%, the sweetening agent from about 0.1% to about 95% and the AFP from about 0.01% to about 0.5%.

In one aspect, the disclosure provides any of Compositions 1 or 2 or 3, et seq. for use in repairing or inhibiting or protection or prevention of dental erosion, promoting remineralization, and/or enhancing the anti-cavity effects of fluoride; for example for use in any of the following methods according to Method 1, et seq.

In another aspect, the disclosure provides a method (Method 1 or 2 or 3) of repairing or inhibiting dental erosion, promoting dental remineralization, and/or enhancing the anti-cavity effects of fluoride comprising applying to the teeth a composition, e.g., any of Composition 1 or 2 or 3, et seq. for example an oral care composition comprising:
a) AFP
b) an orally acceptable carrier,
wherein the AFP is present in the composition in an amount of from 0.01 weight % to 3 weight % by total weight of the composition. For example, the disclosure provides:
1.1. Method 1 wherein the AFP is an insect AFP.
1.2. Method 1 wherein the AFP has the polypeptide sequence SEQ ID NO:2 . . . .
1.3. Method 2 wherein the AFP is a plant AFP.
1.4. Method 2 wherein the AFP has the polypeptide sequence SEQ ID NO:3 . . . .
1.5. Method 3 wherein the AFP is a fish AFP.
1.6. Method 3 wherein the AFP has the polypeptide sequence SEQ ID NO:1 . . . .
1.7. Any foregoing Method wherein the AFP comprises fluoride.
1.8. Any foregoing Method wherein the partially hydrolyzed plant protein has been neutralized to approximately neutral or slightly basic pH, e.g., pH 7-8, e.g., using a phosphate buffer.
1.9. Any foregoing Method wherein the AFP comprises a biocide, e.g., cetylpyridinium chloride (CPC) at an effective concentration, e.g., 0.1% by weight of the filtrate.
1.10. Any foregoing Method wherein the AFP is present in the composition in an amount of from 0.01 weight % to 3 weight % by total weight of the composition, e.g., 0.01 weight % to 2 weight %, e.g., about 0.02 weight %, about 0.1 weight %, about 0.5 weight % or about 2 weight percent by total weight of the composition.
1.11. Any foregoing composition wherein the Composition comprises an effective amount of fluoride.
1.12. Any foregoing Method wherein the amount of fluoride is 100 ppm to 1000 ppm, for example about 500 ppm fluoride.
1.13. Any foregoing Method wherein the composition is in a form selected from a mouthrinse, a toothpaste, a tooth gel, a tooth powder, a non-abrasive gel, a mousse, a foam, a mouth spray, and a tablet.
1.14. Any foregoing Method, wherein the composition further comprises one or more agents selected from: abrasives, pH modifying agents, surfactants, foam modulators, thickening agents, viscosity modifiers, humectants, anti-calculus or tartar control agents, sweeteners, flavorants and colorants.
1.15. Any foregoing Method wherein the composition is a dentifrice, e.g., a toothpaste.
1.16. Any foregoing Method wherein the composition is selected from any of Compositions 1 or 2 or 3, et seq., supra.
1.17. Any foregoing Method which is a method for reducing, inhibiting or repairing dental erosion, for example erosion of the enamel, for example wherein the composition is applied to the teeth of a patient having been identified as having dental erosion or being at elevated risk of having dental erosion.
1.18. Any foregoing Method which is a method for promoting dental remineralization, for example remineralization of the enamel, for example wherein the composition is applied to the teeth of a patient having been identified as having demineralization.
1.19. Any foregoing Method which is a method for enhancing the anti-cavity effects of fluoride, for example wherein the composition is applied to the teeth of a patient having been identified as having early signs of tooth decay, for example early enamel caries, or as having active decay, or as being at elevated risk of tooth decay.
1.20. Method 1.15 wherein the composition comprises an effective amount of fluoride and/or wherein the method further comprises administration of an oral care product comprising an effective amount of fluoride mouth rinse or toothpaste comprising an effective amount of fluoride.

In another embodiment, the disclosure provides the use of an AFP in the manufacture of an oral care composition, for example according to any of Compositions 1 or 2 or 3, et seq. for repairing or inhibiting dental erosion, promoting remineralization, and/or enhancing the anti-cavity effects of fluoride, e.g., in any of Methods 1 or 2 or 3, et seq.

In another aspect, the disclosure provides a method (Method 4) of making an oral care product, e.g. an oral care product useful for repairing or inhibiting dental erosion, promoting dental remineralization, and/or enhancing the anti-cavity effects of fluoride, e.g., a product according to any of Composition 1 or 2 or 3, et seq., comprising
a) neutralizing an AFP by dilution with an aqueous buffer solution, e.g., a phosphate buffer solution, to obtain a solution having approximately neutral or slightly basic pH, e.g., pH 7-8;
b) filtering and centrifuging the solution product of a) to obtain a filtrate comprising the AFP;
c) adding fluoride (e.g., in the form of an orally acceptable salt containing fluoride, for example sodium fluoride or sodium monofluorophosphate), and optionally a biocide (e.g., cetylpyridinium chloride at an effective amount, e.g., 0.01 to 1%, e.g., about 0.1% by weight of the filtrate) to the filtrate product of b);
d) admixing the product of c) to components of an orally acceptable carrier to obtain an oral care composition comprising the AFP in an amount of from 0.01 weight % to 3 weight % by total weight of the composition.

For example, the disclosure provides an oral care composition comprising AFP, e.g., a composition according to any of Composition 1 or 2 or 3, et seq., wherein the oral care composition is obtained or obtainable by the process of Method 4, et seq.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 shows ice crystal formation in the presence and absence of AFP.

FIG. 2 shows repair efficacy of BM80 on low and high concentration using roughness assay.

FIG. 3 shows repair efficacy (nanohardness) of AFP using nanoindentation.

FIG. 4 shows repair efficacy (using Young's modulus) of AFP using nanoindentation.

FIG. 5 shows repair efficacy of AFP using microhardness.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Antifreeze Proteins (AFPs)

Antifreeze Proteins (AFPs) are proteins from organisms such as certain vertebrates, plants, fungi and bacteria that permit their survival in subzero environments. AFPs are also called Ice structuring proteins. AFPs bind to small ice crystals to inhibit growth and recrystallization of ice that would otherwise be fatal for the organisms. The common feature of AFPS is a thermal hysteresis, which is a difference between the melting point and the freezing point. The addition of AFPS at the interface between solid ice and liquid water inhibits the thermodynamically favored growth of the ice crystal. Ice growth is kinetically inhibited by the AFPs covering the water-accessible surfaces of ice. Thermal hysteresis is easily measured in the lab with a nanolitre osmometer.

There is no common consensus sequence of the AFPs from the different organisms Crit Rev Biotechnol. 2008; 28: 57-82., Properties, potentials, and prospects of antifreeze proteins, Venketesh S1, Dayananda C.; Journal of Experimental Biology 2015; 218: 1846-1855., Animal ice-binding (antifreeze) proteins and glycolipids: an overview with emphasis on physiological function, John G Duman.

Useful for the instant invention are AFPs from fish such as e.g. macrozoarces *americanus* or from plants such as *Lolium perenne*. Preferred AFPs are such from insects. There are two known types of insect AFPs, *Tenebrio* and *Dendroides* AFPs which are both in different insect families. They are similar to one another, and consist of varying numbers of 12 or 13-mer repeats of approximately 8.3-12.5 kD. Especially preferred AFPs from insects are those from *choristoneura fumiferana.*

Especially preferred AFPs are those with the following polypeptide sequence:
BM 82 (SEQ ID NO:1),
BM 80 (SEQ ID NO:2),
BM 83 (SEQ ID NO:3), Particularly preferred embodiments of the present invention are proteins having the polypeptide sequences depicted in SEQ ID NO: 1, 2, 3. Particularly preferred embodiments are also proteins which arise from substitution, insertion or deletion of at least one, two, up to 10, preferably 5, amino acids. Particularly preferred are proteins where up to 1%, up to 3%, up to 5%, of all, amino acids, starting from the polypeptide sequences depicted in SEQ ID NO: 1, 2, 3, are substituted or deleted and which still have at least 50% preferably at least 80% and most preferred at least 90% of the biological property of the starting proteins. Biological property of the proteins here means the thermal hysteresis.

The AFPs can also be linked to a fusion partner, preferably at the amino- or at carboxyterminal part of the AFP. A fusion partner can be e.g. a small peptide sequence such as a his-tag—a sequence of 6 to 10 his residues—, which is useful for purification of the AFP. SEQ ID NO: 1, 2 or 3, e.g. have at their carboxyterminus a hiss tag.

A fusion partner can also be some additional amino acids at the amino- and or at the carboxyterminus of the AFP which are the result of either newly creating or inactivating recognition sites for restriction endonucleases at the nucleic acid level.

The AFPs can also be linked to a fusion partner, preferably at the amino- or at carboxyterminal part of the AFP. A fusion partner can be e.g. a small peptide sequence such as hydroxyapatite binding peptides, preferably one having a peptide sequence disclosed in SEQ ID NO:4 to SEQ ID NO:19

|  | SEQ ID NO: 4 |
|---|---|
| IDDYTRA | |
| HPPLHHA | SEQ ID NO: 5 |
| SPSTHWK | SEQ ID NO: 6 |
| GSPATAA | SEQ ID NO: 7 |
| GKVQAQS | SEQ ID NO: 8 |
| YPVTPSI | SEQ ID NO: 9 |
| IPTLPSS | SEQ ID NO: 10 |
| YQGASEN | SEQ ID NO: 11 |
| EHITTSN | SEQ ID NO: 12 |
| RILITIP | SEQ ID NO: 13 |
| IPITNLR | SEQ ID NO: 14 |

TTSTRHI                SEQ ID NO: 15

NERALTL                SEQ ID NO: 16

MQTVEVT                SEQ ID NO: 17

SWGTQTD                SEQ ID NO: 18

TLPASSV                SEQ ID NO: 19

Preferred embodiments of AFP linked to a hydroxyapatite binding peptide is SEQ ID NO:20 which is a fusion of SEQ NO:4 and SEQ ID NO:2, and SEQ ID NO:21, which is a fusion of SEQ ID NO:10 and SEQ ID NO:2

AFP in the sense of this invention can also mean that multiple copies (i.e. multimers) of an AFP are fused together, e.g. two or three AFP—having the identical structure (i.e. homomers) or a different structure (i.e. heteromers)—form a "super AFP". E.g. a AFP from fish can be fused together with an AFP from insects or two identical fish AFP are fused together.

AFP in the sense of this invention can also mean that an AFP is linked to a non-peptidic molecule such as a pharmaceutical drug, a vitamin or a flavoring. By this a non-peptidic molecule can be targeted to the dental enamel via the AFP part. The linkage of the non-peptidic molecule to the AFP is possible e.g. by reaction with the side chains of the amino acids of the AFP such as OH of Ser or Thr or SH of Cys or Met or COOH of Asp or Glu or $NH_2$ of Lys or Arg. The chemical linkage can be a "permanent" one, i.e. one that is not hydrolyzed by the saliva or it can be a "labile" one, i.e. one that is susceptible to cleavage by the saliva.

AFPs influence the ice crystal formation and also the shape of the ice crystals which can be seen in microscopy when ice crystals formed in presence of AFP are compared with ice crystals without AFP. If bioactive AFP is present the ice crystals have a sharp appearance compared with the round, droplet-like appearance of the crystals formed without AFP. This can also be used to determine the biological activity of AFPs.

See FIG. 1 ice crystal formation in the presence and absence of AFP. (Water means distilled water without AFP).

The AFPs can be manufactured chemically by known methods of peptide synthesis, for example solid phase synthesis according to Merrifield.

Particularly useful, however, are genetic methods for manufacturing in which nucleic acid sequences, in particular DNA sequences, coding for the AFP and—if wished—one or more fusion partner are combined in such a way that gene expression of the combined nucleic acid sequence generates the desired protein in a host organism.

Suitable host organisms (producer organisms) here may be prokaryotes (including Archaea) or eukaryotes, particularly bacteria including halobacteria and methanococci, fungi, insect cells, plant cells and mammalian cells, particularly preferably Escherichia coli, Bacillus subtilis, Bacillus megaterium, Aspergillus oryzea, Aspergillus nidulans, Aspergillus niger, Pichia pastoris, Pseudomonas spec., Lactobacillen, Hansenula polymorpha, Trichoderma reesei, SF9 (or related cells), and others.

The invention moreover relates to expression constructs comprising a nucleic acid sequence coding for a polypeptide of the invention under the genetic control of regulatory nucleic acid sequences, and also vectors comprising at least one of said expression constructs.

Preference is given to such constructs of the invention comprising a promoter 5' upstream of the particular coding sequence and a terminator sequence 3' downstream, and also, if appropriate, further customary regulatory elements, in each case operatively linked to said coding sequence.

An "operative linkage" means the sequential arrangement of promoter, coding sequence, terminator and, if appropriate, further regulatory elements in such a way that each of the regulatory elements is able to fulfill its function in accordance with its intended use in connection with expressing the coding sequence.

Examples of sequences which can be operatively linked are targeting sequences and also enhancers, polyadenylation signals and the like. Further regulatory elements comprise selectable markers, amplification signals, origins of replication and the like. Examples of suitable regulatory sequences are described in Goeddel, Gene Expression Technology: Methods in Enzymology 185, Academic Press, San Diego, Calif. (1990).

In addition to these regulatory sequences, the natural regulation of these sequences may still be present upstream of the actual structural genes and, if appropriate, have been genetically modified such that the natural regulation has been switched off and expression of the genes has been increased.

A preferred nucleic acid construct advantageously also comprises one or more of the enhancer sequences already mentioned which are functionally linked to the promoter and enable expression of the nucleic acid sequence to be increased. Additional advantageous sequences such as further regulatory elements or terminators may also be inserted at the 3' end of the DNA sequences.

The nucleic acids of the invention may be present in the construct in one or more copies. The construct may comprise still further markers such as antibiotic resistances or genes which complement auxotrophies, for selecting for the construct, if appropriate.

Examples of regulatory sequences which are advantageous for the method of the invention are present in promoters such as the cos, tac, trp, tet, trp-tet, Ipp, lac, Ipp-lac, laclq-T7, T5, T3, gal, trc, ara, rhaP(rhaPBAD) SP6, lambda-PR or lambda-P promoter, which are advantageously used in Gram-negative bacteria. Further examples of advantageous regulatory sequences are present in the Gram-positive promoters amy and SP02, in the yeast or fungal promoters ADC1, MFalpha, AC, P-60, CYC1, GAPDH, TEF, rp28, ADH. It is also possible to use artificial promoters for regulation.

To be expressed in a host organism, the nucleic acid construct is advantageously inserted into a vector such as, for example, a plasmid or a phage, which enables the genes to be expressed optimally in the host. Apart from plasmids and phages, vectors also mean any other vectors known to the skilled worker, i.e., for example, viruses such as SV40, CMV, baculovirus and adenovirus, transposons, IS elements, phasmids, cosmids, and linear or circular DNA and also the Agrobacterium system.

These vectors may either replicate autonomously in the host organism or be replicated chromosomally. These vectors constitute another embodiment of the invention. Examples of suitable plasmids are pLG338, pACYC184, pBR322, pUC18, pUC19, pKC30, pRep4, pHS1, pKK223-3, pDHE19.2, pHS2, pPLc236, pMBL24, pLG200, pUR290, pIN-III"3-B1, tgt11 or pBdCl in E. coli, pIJ101, pIJ364, pIJ702 or pIJ361 in Streptomyces, pUB110, pC194 or pBD214 in *Bacillus*, pSA77 or pAJ667 in *Corynebacterium*, pALS1, pIL2 or pBB116 in fungi, 2alpha, pAG-1, YEp6, YEp13 or pEMBLYe23 in yeasts or pLGV23, pGHlac+, pBIN19, pAK2004 or pDH51 in plants. Said plasmids are a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018).

Advantageously, the nucleic acid construct additionally comprises, for the purpose of expressing the other genes present, also 3'- and/or 5'-terminal regulatory sequences for increasing expression which are selected for optimal expression depending on the host organism and gene or genes selected.

These regulatory sequences are intended to enable the genes and protein expression to be expressed specifically. Depending on the host organism, this may mean, for example, that the gene is expressed or overexpressed only after induction or that it is expressed and/or overexpressed immediately.

In this connection, the regulatory sequences or factors may preferably have a beneficial influence on, and thereby increase, gene expression of the introduced genes. Thus the regulatory elements can advantageously be enhanced at the transcriptional level by using strong transcription signals such as promoters and/or enhancers. Apart from that, however, it is also possible to enhance translation by improving mRNA stability, for example.

In another embodiment of the vector, the vector comprising the nucleic acid construct of the invention or the nucleic acid of the invention may also advantageously be introduced in the form of a linear DNA into the microorganisms and integrated into the genome of the host organism by way of heterologous or homologous recombination. Said linear DNA may consist of a linearized vector such as a plasmid, or only of the nucleic acid construct or the nucleic acid of the invention.

In order to achieve optimal expression of heterologous genes in organisms, it is advantageous to modify the nucleic acid sequences according to the specific codon usage employed in the organism. The codon usage can be readily determined on the basis of computer analyses of other known genes of the organism in question.

An expression cassette of the invention is prepared by fusing a suitable promoter to a suitable coding nucleotide sequence and a terminator signal or polyadenylation signal. For this purpose, use is made of familiar recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables the genes to be expressed optimally in the host. Vectors are well known to the skilled worker and can be found, for example, in "Cloning Vectors" (Pouwels P. H. et al., Eds. Elsevier, Amsterdam-New York-Oxford, 1985).

The vectors of the invention can be used to prepare recombinant microorganisms which are transformed, for example, with at least one vector of the invention and may be used for producing the polypeptides of the invention. Advantageously, the above-described recombinant constructs of the invention are introduced into and expressed in a suitable host system. Preference is given here to using common cloning and transfection methods known to the skilled worker, such as, for example, coprecipitation, protoplast fusion, electroporation, retroviral transfection and the like, in order to express said nucleic acids in the particular expression system. Suitable systems are described, for example, in Current Protocols in Molecular Biology, F. Ausubel et al., Eds. Wiley Interscience, New York 1997, or Sambrook et al. Molecular Cloning: A Laboratory Manual, 2nd Ed., Cold Spring Harbor Laboratory, Cold Spring Harbor Laboratory Press, Cold Spring Harbor, N.Y., 1989.

It is also possible according to the invention to prepare homologously recombined microorganisms. For this purpose, a vector is prepared which comprises at least one section of a gene of the invention or of a coding sequence, into which, if appropriate, at least one amino acid deletion, addition or substitution has been introduced in order to modify, for example functionally disrupt, the sequence of the invention (knockout vector). The introduced sequence may, for example, also be a homolog from a related microorganism or be derived from a mammalian, yeast or insect source. The vector used for homologous recombination may alternatively be designed such that the endogenous gene mutates or is modified in some other way during homologous recombination but still encodes the functional protein (for example, the upstream regulatory region may have been modified in a way which modifies expression of the endogenous protein). The modified section of the gene of the invention is in the homologous recombination vector. The construction of suitable vectors for homologous recombination is described, for example, in Thomas, K. R. and Capecchi, M. R. (1987) Cell 51: 503.

Any prokaryotic or eukaryotic organisms are in principle suitable for being used as recombinant host organisms for the nucleic acid of the invention or to the nucleic acid construct. Advantageously used host organisms are microorganisms such as bacteria, fungi or yeasts. Gram-positive or Gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia*, *Pseudomonas*, *Streptomyces*, *Nocardia*, *Burkholderia*, *Salmonella*, *Agrobacterium* or *Rhodococcus*, are advantageously used.

Depending on the host organism, the organisms used in the method of the invention are grown or cultured in a manner known to the skilled worker. Microorganisms are usually grown in a liquid medium comprising a carbon source usually in the form of sugars, a nitrogen source usually in the form of organic nitrogen sources such as yeast extract or salts such as ammonium sulfate, trace elements such as iron, manganese, magnesium salts, and, if appropriate, vitamins, at temperatures of between 0 and 100° C., preferably between 10 and 60° C., while being gassed with oxygen. The pH of the nutrient liquid may or may not be maintained here at a fixed value, i.e. regulated during growth. Growth may take place batch-wise, semibatch-wise or continuously. Nutrients may be introduced initially at the beginning of the fermentation or be subsequently fed in semicontinuously or continuously. The enzymes may be isolated from the organisms using the method described in the examples or be used for the reaction as a crude extract.

The invention furthermore relates to methods of recombinantly producing polypeptides of the invention or functional, biologically active fragments thereof, which methods comprise culturing a polypeptide-producing microorganism, if appropriate inducing expression of said polypeptides and isolating them from the culture. In this way the polypeptides may also be produced on an industrial scale if desired. The recombinant microorganism may be cultured and fermented by known methods. For example, bacteria can be propagated in TB medium or LB medium and at a temperature of from 20 to 40° C. and a pH of from 6 to 9. Suitable culturing conditions are described in detail in, for example, T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is isolated from the lysate by known methods of isolating proteins. The cells may optionally be disrupted by high-frequency ultrasound, by high pressure, for example in a French pressure cell, by osmolysis, by the action of detergents, lytic enzymes or organic solvents, by using homogenizers or by a combination of several of the methods listed.

The polypeptides may be purified by means of known, chromatographic methods such as molecular sieve chromatography (gel filtration), such as Q-Sepharose chromatography, ion exchange chromatography and hydrophobic chromatography, and also by means of other customary methods such as ultrafiltration, crystallization, salting out, dialysis and native gel electrophoresis. Suitable methods are described, for example, in Cooper, F. G., Biochemische Arbeitsmethoden [original title: The tools of biochemistry], Verlag Water de Gruyter, Berlin, N.Y. or in Scopes, R., Protein Purification, Springer Verlag, New York, Heidelberg, Berlin.

It may be advantageous, for the purpose of isolating the recombinant protein, to use vector systems or oligonucleotides which extend the cDNA by particular nucleotide sequences and thereby encode altered polypeptides or fusion proteins which facilitate purification, for example. Examples of such suitable modifications are "tags" acting as anchors, for example the modification known as hexahistidine anchor, or epitopes which can be recognized by antibodies as antigens (described, for example, in Harlow, E. and Lane, D., 1988, Antibodies: A Laboratory Manual. Cold Spring Harbor (N.Y.) Press). Further suitable tags are, for example, HA, calmodulin-BD, GST, MBD; chitin-BD, streptavidin-BD-Avi tag, Flag tag, T7, etc. These anchors may be used for attaching the proteins to a solid support, such as, for example, a polymer matrix which may have been introduced into a chromatographic column, for example, or to a microtiter plate or any other support. The corresponding purification protocols can be obtained from the commercial affinity tag suppliers.

In some embodiments, the AFP is present in the composition in an amount of from 0.01 weight % to 3 weight % by total weight of the composition. In some embodiments, the AFP is present in the composition in an amount of from 0.01 weight % to 3 weight %, or from 0.01 weight % to 2 weight %, or from 0.02 weight % to 1 weight % by total weight of the composition. In other embodiments, the AFP is present in the composition in an amount of from 0.01 weight % to 1 weight %, or from 0.021 weight % to 0.5 by total weight of the composition In further embodiments, the AFP is present in the composition in an amount of from 0.05 weight % to 3 weight %, or from 0.05 weight % to 2 weight %, or from 0.05 weight % to 1 weight % by total weight of the composition.

Orally Acceptable Carrier and Optional Ingredients

The expression "orally acceptable carrier" as used herein denotes a carrier made from materials that are safe and acceptable for oral use in the amounts and concentrations intended, for example materials as would be found in conventional toothpaste and mouthwash. Such materials include water or other solvents that may contain a humectant such as glycerin, sorbitol, xylitol and the like. In some aspects, the term "orally acceptable carrier" encompasses all of the components of the oral care composition except for the hydrolyzed plant protein and the fluoride. In other aspects, the term refers to inert or inactive ingredients that serve to deliver the AFP, and/or any other functional ingredients, to the oral cavity.

Orally acceptable carriers for use in the invention include conventional and known carriers used in making mouth rinses or mouthwashes, toothpastes, tooth gels, tooth powder, lozenges, gums, beads, edible strips, tablets and the like. Carriers should be selected for compatibility with each other and with other ingredients of the composition.

The following non-limiting examples are provided. In a toothpaste composition, the carrier is typically a water/humectant system that provides a major fraction by weight of the composition. Alternatively, the carrier component of a toothpaste composition may comprise water, one or more humectants, and other functional components other than the AFP. In a mouth rinse or a mouthwash formulation, the carrier is typically a water/alcohol liquid mixture in which the AFP is dissolved or dispersed. In a dissolvable lozenge, the carrier typically comprises a solid matrix material that dissolves slowly in the oral cavity. In chewing gums, the carrier typically comprises a gum base, while in an edible strip, the carrier typically comprises one or more film forming polymers.

The oral care compositions provided herein may further comprise one or more additional ingredients selected from abrasives, pH modifying agents, surfactants, foam modulators, thickening agents, viscosity modifiers, humectants, anti-calculus or tartar control agents, sweeteners, flavorants, colorants and preservatives. These ingredients may also be regarded as carrier materials. Non-limiting examples are provided below.

In one embodiment a composition of the invention comprises at least one abrasive, useful, for example, as a polishing agent. Any orally acceptable abrasive can be used, but the type, fineness (particle size) and amount of abrasive should be selected so that tooth enamel is not excessively abraded during normal use of the composition. Suitable abrasives include, without limitation, silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, [beta]-calcium pyrophosphate, tricalcium phosphate, calcium polymetaphosphate and insoluble sodium polymetaphosphate. One or more abrasives are optionally present in the oral care compositions of the present invention in an amount of 1 weight % to 5 weight % by total weight of the composition. The average particle size of an abrasive, if present, is generally 0.1 to 30 μm, and preferably, 5 to 15 μm.

In a further embodiment an oral care composition of the invention comprises at least one bicarbonate salt, useful, for example, to impart a "clean feel" to teeth and gums due to effervescence and release of carbon dioxide. Any orally acceptable bicarbonate can be used, including, without limitation, alkali metal bicarbonates such as sodium and potassium bicarbonates, ammonium bicarbonate and the like. One or more bicarbonate salts are optionally present in a total amount of 1 weight % to 10% by weight of the composition.

In a still further embodiment, an oral care composition of the invention comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments a pH of 2 to 8, 3 to 9, 4 to 8, 5 to 7, 6 to 10, or 7 to 9. Any orally acceptable pH modifying agent can be used, including, without limitation, carboxylic, phosphoric and sulfonic acids, acid salts (for example, monosodium citrate, disodium citrate, monosodium malate), alkali metal hydroxides such as sodium hydroxide, carbonates such as sodium carbonate, bicarbonates, borates, silicates, phosphates (for example, monosodium phosphate, trisodium phosphate, pyrophosphate salts) imidazole and the like. One or more pH modifying agents are optionally present in a total amount effective to maintain the composition in an orally acceptable pH range.

In a still further embodiment a composition of the invention comprises at least one surfactant, useful, for example, to provide enhanced stability to the composition and the components contained therein, to aid in cleaning a dental surface through detergent action, and to provide foam upon agitation (for example, during brushing with a dentifrice composition of the invention). Any orally acceptable surfactant, including those which are anionic, nonionic or amphoteric, can be used. Suitable anionic surfactants include, without limitation, water-soluble salts of $C_{8-20}$ alkyl sulfates, sulfonated monoglycerides of $C_{8-20}$ fatty acids, sarcosinates, taurates and the like. Suitable nonionic surfactants include, without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01 weight % to 10 weight %, for example, from 0.05 weight % to 5 weight % or from 0.1 weight % to 2 weight % by total weight of the composition.

In a still further embodiment, an oral care composition of the invention comprises at least one foam modulator, useful, for example, to increase the amount, thickness or stability of foam generated by the composition upon agitation. Any orally acceptable foam modulator can be used including, without limitation, polyethylene glycols (PEGs). One or more PEGs are optionally present in a total amount of from 0.1 weight % to 10 weight by total weight of the composition.

In a still further embodiment, an oral care composition of the invention comprises at least one thickening agent, useful, for example, to impart a desired consistency and/or mouth feel to the composition. Any orally acceptable thickening agent can be used including, without limitation, carbomers (carboxyvinyl polymers), carrageenans, cellulosic polymers such as hydroxyethylcellulose, carboxymethylcellulose (CMC) and salts thereof, natural gums such as karaya, xanthan, gum arabic and tragacanth, colloidal magnesium aluminum silicate, colloidal silica and the like. One or more thickening agents are optionally present in a total amount of 0.01 weight % to 15 weight %, by total weight of the composition.

In a still further embodiment a composition of the invention comprises at least one viscosity modifier, useful, for example, to inhibit settling or separation of ingredients or to promote re-dispersion of ingredients upon agitation of a liquid composition. Any orally acceptable viscosity modifier can be used including, without limitation, mineral oil, petrolatum, clays, silica and the like. One or more viscosity modifiers are optionally present in a total amount of 0.01 weight % to 10 weight %, by total weight of the composition.

In a still further embodiment, an oral care composition of the invention comprises at least one humectant which may be used to prevent hardening of a toothpaste upon exposure to air. Any orally acceptable humectant can be used, including, without limitation, polyhydric alcohols such as glycerin, sorbitol, xylitol or low molecular weight PEGs. Most humectants also function as sweeteners. One or more humectants are optionally present in a total amount of 1 weight % to 50 weight % by total weight of the composition.

In a still further embodiment, an oral care composition of the invention comprises at least one sweetener which enhances taste of the composition. Any orally acceptable natural or artificial sweetener can be used including, without limitation, dextrose, sucrose, maltose, dextrin, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount of 0.005 weight % to 5 weight % by total weight of the composition.

In a still further embodiment, an oral care composition of the invention comprises at least one flavorant which enhances the taste of the composition. Any orally acceptable natural or synthetic flavorant can be used including, without limitation, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences, and the like. Also encompassed within flavorants are ingredients that provide fragrance and/or other sensory effects in the mouth, including cooling or warming effects. Such ingredients illustratively include menthol, menthyl acetate, menthyl lactate, camphor, eucalyptus oil, eucalyptol, eugenol, cassia, oxanone, α-irisone, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01 weight % to 5 weight %, by total weight of the composition.

In a still further embodiment, an oral care composition of the invention comprises at least one colorant. A colorant can serve a number of functions. These include providing a white or light-colored coating on a dental surface, indicating locations on a dental surface that have been effectively contacted by the composition, and/or modifying the appearance of the composition to enhance attractiveness to the consumer. Any orally acceptable colorant can be used including, without limitation, talc, mica, magnesium carbonate, calcium carbonate, magnesium silicate, magnesium aluminum silicate, silica, titanium dioxide, zinc oxide, iron oxide, ferric ammonium ferrocyanide, manganese violet, titaniated mica, bismuth oxychloride and the like. One or more colorants are optionally present in a total amount of 0.001 weight % to 20 weight % by total weight of the composition.

In a still further embodiment, an oral care composition of the invention comprises a preservative. The preservative may be selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of from about 0.001 to about 1 weight %, by total weight of the composition.

The following examples illustrate compositions of the invention and their uses. The exemplified compositions are illustrative and do not limit the scope of the invention.

EXAMPLES

Example 1—Surface Roughness

Bovine teeth are cut, ground and polished to obtain enamel blocks having approximate dimensions of 3 mm×3 mm×2 mm. The thickness of the enamel is approximately 1 to 2 mm, and the thickness of dentin is approximately 1 mm. All measurements are taken on the enamel surface.

The surface roughness of enamel blocks is measured before and after acid etching. Acid etching is achieved by placing the enamel blocks in 1% citric acid solution (pH 3.8) until the surface roughness (Sq) reaches 100-200. This Sq value is recorded as the surface roughness of etched enamel. (Sq is a standard measurement defined in ISO 25178 basically as the root mean square height relative to the arithmetical mean height of the surface being measured, so it corresponds to the mean of all absolute distances of the profile from the center plane within the measuring area, such that if it is higher, it means that that there are more pronounced peaks and valleys on the surface, i.e., the surface is rougher, and if it is lower, the surface is smoother.) The AFP is diluted to the final concentration using a $Na_2HPO_4$ buffer (1.5 mM) and $CaCl_2$) (2.5 mM). After neutralizing to a pH of 7.5, the solution is filtered and centrifuged. Acid-etched enamel blocks are subsequently incubated with a solution comprising the treated AFP at a concentration of 5.5 µM or 55 µM (2 ml solution per block) for 60 minutes.

After the 60 minute incubation period, the enamel blocks are incubated in artificial saliva (AS) solution (0.4 g NaCl, 0.4 g KCl, 0.8 g $CaCl_2$, 0.69 g $NaH_2PO_4$, 1 g urea, 1 liter distilled water; pH 7 (adjusted using 1M NaOH)) for 22 hours. The enamel blocks are then treated a second time with AFP, and incubated again with artificial saliva for 22 hours. The blocks are then rinsed with deionized (DI) water and air-dried prior to measuring their surface roughness. Enamel blocks treated with 0.5% PBS are used as a negative control for the experiment. The results are illustrated in Table 1. The % repair represents the % reduction in surface roughness (Sq) achieved by protein treatment, relative to the surface roughness of (untreated) acid-etched enamel.

TABLE 1

Results of surface roughness assay

| Test solution | Mean % remineralization |
|---|---|
| 5.5 pM AFP 80 = SEQ ID NO 2 | 14% |
| 55 pM AFP 80 = SEQ ID NO 2 | 24 |
| PBS | −4% |

See FIG. 2 Repair efficacy of BM80 on low and high concentration using roughness assay As indicated in Table 1, AFP SEQ ID NO2 is effective in reducing the surface roughness of acid-etched enamel blocks at a concentration of 5.5 res. 55 µM

Example 2—Nanoindentation

Enamel blocks are prepared as described in Example 1. Acid-etching is achieved by placing the enamel blocks in 1% citric acid solution (pH 3.8) for 15 minutes. The nanohardness and Young's modulus at 500 nm depth are measured prior to and after etching. Etched enamel blocks are incubated with a solution of the AFPs SEQ ID NO: 20, at a concentration of 20 µM for 30 minutes (2 ml solution/block), followed by an incubation with AS solution as described in Example 1, for 22 to 24 hours. The AFP and AS incubation steps are repeated two additional times, after which the enamel blocks are rinsed with DI water and air-dried. The nanohardness and Young's modulus of the treated enamel blocks are measured at 500 nm depth to assess the enamel repair effects of the AFP. A solution of 500 ppm fluoride is used as a positive control for the experiment. The results are illustrated in Tables 2 and 3.

TABLE 2

Repair efficacy of AFP—nanohardness

| Test | Nanohardness Repair at 500 nm depth (%) |
|---|---|
| AFP SEQ ID NO 20 = BM133 | 38 |
| Fluoride (control) | 31 |

TABLE 3

Repair efficacy of hydrolyzed wheat protein—Young's modulus

| Test | Young's Modulus Repair at 500 nm depth (%) |
|---|---|
| AFP SEQ ID NO: 20 = BM133 | 63 |
| Fluoride (control) | 48 |

See FIG. 3 Repair efficacy (nanohardness) of AFP using nanoindentation

See FIG. 4 Repair efficacy (using Young's modulus) of AFP using nanoindentation

As can be seen in Tables 2 and 3, AFP is effective in repairing acid-eroded enamel.

Example 3—Microhardness

Enamel blocks are prepared as described in Example 1. Microhardness is measured using a Micromet 6020 Microhardness Tester with a Knoop Diamond Indenter and a 50 g load (Buehler, Lake Bluff, Ill., USA). Blocks with a Knoop hardness (KH) of at least 300 are selected. The blocks are etched by immersing in 30% phosphoric acid for 15 seconds. The KH on the left and right sides of the blocks are measured. Subsequently, the right side of the blocks are covered with tape prior to treating the blocks with 20 mg/ml solution of AFP, each neutralized as described in example 1, for two terms of 30 minutes. (The tape on the right hand side of the blocks prevents exposure of this side to the protein solution and serves as an internal control). The blocks are washed twice with DI water @ 5 minutes, 500 PRM between the two treatments and after the second treatment. Subsequently, the tape is removed and the blocks are incubated in AS solution (0.2 mM $MgCl_2$, 1 mM $CaCl_2.H_2O$, 20 mM HEPES buffer, 4 mM $KH_2PO_4$, 16 mM KCl, 4.5 mM $NH_4Cl$, 300 ppm NaF, 0.05 wt. % $NaN_3$, at pH 7 (adjusted with 1M NaOH)) for 7 days. After rinsing the enamel blocks with DI water and air-drying the rinsed blocks, microhardness is measured again. Surface microhardness regain (SMHL, Remin %) as a percent is calculated as ((Microhardness$_{repaired}$−Microhardness$_{etched}$)/(Microhardness$_{sound}$−Microhardness$_{etched}$))*100. The results of the microhardness assay are illustrated in Table 4.

TABLE 4

Results of microhardness assay

| Protein | % remineralization (mean) |
|---|---|
| AFP SEQ ID NO: 2 = BM80 | 36% |
| AFP SEQ ID NO: 20 = BM133 | 38% |
| AFP SEQ ID NO: 21 = BM135 | 20 |
| Control buffer | 1% |

See FIG. 5 Repair efficacy of AFP using microhardness

It can be seen from Table 4 that all AFPs are effective in remineralizing the enamel surface of acid-etched enamel blocks. Note that for all of the microhardness tests, the reminineralization percentage from the right/internal control side, which was immersed artificial *salvia* as well and had some repair from artificial *salvia*, is subtracted from the results, so that the data present the differential effect of the AFP.

While particular embodiments of the invention have been illustrated and described, it will be obvious to those skilled in the art that various changes and modifications may be made without departing from the scope of the invention as defined in the appended claims.

The invention claimed is:

1. A method of repairing or inhibiting or protection against or prevention of dental erosion, promoting dental remineralization, and/or enhancing the anti-cavity effects of fluoride comprising applying to the teeth an oral care composition comprising:
   a) an antifreeze protein (AFP); and
   b) an orally acceptable carrier,
   wherein AFP has the polypeptide sequence as set forth in SEQ ID NO: 1, SEQ ID NO: 2 or SEQ ID NO: 3, or a polypeptide sequence which arise from substitution, insertion or deletion of up to 5% of all amino acids, starting from the polypeptide sequence as set forth in SEQ ID NO: 1, SEQ ID NO: 2 or SEQ ID NO: 3, and which still has at least 50% of the biological property of the starting protein, and wherein AFP is present in the composition in an amount of from 0.01 weight % to 3 weight % by total weight of the composition.

2. The method of claim 1 wherein the AFP is coupled to a hydroxyapatite binding peptide which is selected from the group formed from SEQ ID NO:4, 5, 6, 7, 8, 9, 10, 11, 12, 13, 14, 15, 16, 17, 18, and 19.

3. The method of claim 1 wherein the AFP is a homomer or heteromer of AFPs and coupled to a hydroxyapatite binding peptide which is selected from the group formed from SEQ ID NO:4, 5, 6, 7, 8, 9, 10, 11, 12, 13, 14, 15, 16, 17, 18, and 19.

4. The method described in claim 1 wherein the oral care composition further comprises an effective amount of fluoride.

5. The method of claim 1 wherein the composition is a dentifrice.

6. The method of claim 1, wherein AFP has the polypeptide sequence as set forth in SEQ ID NO: 1, SEQ ID NO: 2 or SEQ ID NO: 3, or a polypeptide sequence which arise from substitution, insertion or deletion of up to 3% of all amino acids, starting from the polypeptide sequence as set forth in SEQ ID NO: 1, SEQ ID NO: 2 or SEQ ID NO: 3 and which still has at least 80% of the biological property of the starting protein, and wherein AFP is present in the composition in an amount of from 0.01 weight % to 3 weight % by total weight of the composition.

7. The method of claim 1, wherein AFP has the polypeptide sequence as set forth in SEQ ID NO: 1, SEQ ID NO: 2 or SEQ ID NO: 3, or a polypeptide sequence which arise from substitution, insertion or deletion of up to 1% of all amino acids, starting from the polypeptide sequence as set forth in SEQ ID NO: 1, SEQ ID NO: 2 or SEQ ID NO: 3 and which still has at least 90% of the biological property of the starting protein, and wherein AFP is present in the composition in an amount of from 0.01 weight % to 3 weight % by total weight of the composition.

8. The method of claim 1, wherein the AFP has the polypeptide sequence of SEQ ID NO: 1.

9. The method of claim 1, wherein the AFP has the polypeptide sequence of SEQ ID NO: 2.

10. The method of claim 1, wherein the AFP has the polypeptide sequence of SEQ ID NO: 3.

* * * * *